United States Patent [19]

Casara

[11] 4,454,156

[45] Jun. 12, 1984

[54] 4-AMINO-HEPTA-5,6-DIENOIC ACID

[75] Inventor: Patrick Casara, Truchtersheim, France

[73] Assignee: Merrell-Toraude et Compagnie, Strasbourg, France

[21] Appl. No.: 492,986

[22] Filed: May 9, 1983

[30] Foreign Application Priority Data

May 17, 1982 [GB] United Kingdom ............... 8214290

[51] Int. Cl.$^3$ ................... C07C 101/28; A61K 31/195
[52] U.S. Cl. ..................................... 424/319; 562/574
[58] Field of Search ......................... 562/574; 424/319

[56] References Cited

U.S. PATENT DOCUMENTS

| 3,960,927 | 6/1976 | Metcalf | 562/574 |
| 4,178,463 | 12/1979 | Gittos | 562/574 |
| 4,326,071 | 4/1982 | Bey | 424/319 |

*Primary Examiner*—Michael L. Shippen
*Attorney, Agent, or Firm*—Gary D. Street; Raymond A. McDonald; William J. Stein

[57] ABSTRACT

(R,S)- and (S)-4-amino-hepta-5,6-dienoic acid are novel inhibitors of gamma-aminobutyric acid transaminase (GABA-T).

6 Claims, No Drawings

4-AMINO-HEPTA-5,6-DIENOIC ACID

FIELD OF THE INVENTION

The invention relates to novel pharmaceutically useful aminoalkadiene derivatives which are in vivo inhibitors of gamma-aminobutyric acid transaminase (GABA-T). The invention provides the compounds per se, pharmaceutical compositions comprising said compounds, methods of medical treatment using said compounds and processes for preparing said compounds.

BACKGROUND OF THE INVENTION

The biotransformation of gamma-aminobutyric acid (GABA) to succinic acid semialdehyde, which is catalyzed by the enzyme GABA-transaminase (GABA-T), is the primary reaction responsible for the catabolism of GABA, an inhibitory neurotransmitter of the central nervous system. It is known that low levels of endogenous GABA are associated with seizure disorders (such as those involved in epilepsy, alcohol withdrawal, or barbiturate withdrawal), with disorders involving involuntary movement (such as those caused by the extrapyrimidal effects of drugs, for example tardive dyskinesia, with certain psychiatric disorders (such as schizophrenia and depression) and with muscle spasticity. Blockade of the transformation of GABA to succinic acid semialdehyde, such as by irreversible inhibition of GABA-T, can elevate GABA levels in the central nervous system (CNS) and, thus provides a means for treating the disorders of the central nervous system associated with low GABA levels.

Certain compounds are known to be irreversible inhibitors of GABA-T and thereby to elevate brain levels of GABA. Examples are 4-aminohex-5-enoic acid ("vinyl GABA") and 4-aminohex-5-ynoic acid ("acetylenic GABA") [See U.S. Pat. Nos. 3,960,927 and 3,959,356; Lippert et al., *Eur. J. Biochem.*, 74, 441 (1977); Lippert et al., *Brain Research Bulletin*, 5, Suppl. 2, 375 (1980); Jung et al., *Journal of Neurochemistry*, 28 717 (1977); Palfreyman et al., *GABA-Neuro-transmitter*, Alfred Benzon Symposium 12; Larsen et al., Editors, Munksgaard, Copenhagen, 1979, pages 432–446; Jung et al., *Biochemical and Biophysical Research Communications*, 67, 301 (1975); and Palfreyman et al., *Biochemical Pharmacology*, 30, 817 (1981]. A further example is 1-acetylene-1,4-butanediamine ("acetylenic putrescine") (see U.S. Pat. No. 4,139,563)

SUMMARY OF THE INVENTION

The present invention is directed to (S)-4-amino-hepta-5,6-dienoic acid or (R,S)-4-amino-hepta-5,6-dienoic acid, or a pharmaceutically acceptable salt thereof.

The names "(S)-allenyl GABA" and "(R,S)-allenyl GABA" used herein refer to (S)-4-amino-hepta-5,6-dienoic acid and (R,S)-4-amino-hepta-5,6-dienoic acid, respectively.

Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as organic carboxylic acids, for example salicylic, maleic, malonic, tartaric, citric and ascorbic acids, and organic sulfonic acids, for example, methane sulfonic acid; and non-toxic salts formed with inorganic or organic bases, such as, hydroxides of alkali metals, for example, sodium, potassium and lithium, alkaline earth metals, for example, calcium and magnesium, light metals of Group III A, for example, aluminium, organic amines, such as, primary, secondary or tertiary amines, for example, cyclohexylamine, ethylamine, methylamino-ethanolamine and piperidine. The salts are prepared by conventional means.

(S)-Allenyl GABA and (R,S)-allenyl GABA in vivo produce irreversible inhibition of GABA-T and can elevate GABA levels significantly in the CNS when administered orally or parenterally to warm blooded animals. Thus, (S)-allenyl GABA and (R,S)-allenyl GABA are useful for treating disorders in warm blooded animals associated with low levels of GABA in the CNS. In particular the compounds are useful as anti-convulsants for the control of seizures involved in epilepsy. Anti-convulsant activity can be demonstrated by means of standard test procedures in laboratory animals against experimentally-induced seizures. For example, (S)-allenyl GABA and (R,S)-allenyl GABA can protect mice against clonic seizures induced by bicuculline, when treated according to the procedure of W. Buckett (*Br.J.Pharm.*, 68, 177 (1980)) and *Journals of Pharmacological Methods*, 5, 35 (1981)). The compounds also can also protect mice and rats against seizures induced by metrazol (clonic and tonic), maximal electroshock (tonic), and/or 3-mercaptopropionic acid (clonic and tonic).

In addition to the anti-convulsant uses, (S)-allenyl GABA and (R,S)-allenyl GABA are useful for treating CNS disorders involving unvoluntary movement, in particular tardive dyskinesia; for treating psychiatric disorders, for example schizophrenia and depression; and/or for treating muscle spasticity. Moreover, the compounds can produce hypothermia, myorelaxation, anorexia, sedation and/or antinociception when administered systemically.

The dosage of (S)-allenyl GABA and (R,S)-allenyl GABA in warm blooded animals will depend upon the species being treated, the particular compound employed, the severity of the condition being treated, and the mode of administration. In general, an effective dosage capable of providing physiological useful elevation of GABA levels in the CNS can be achieved in warm blooded animals at a dose of from about 1 to about 500 mg/kg (body weight) per day administered orally or parenterally. For larger animals (about 70 kg), a dosage of about 5 to about 100 mg/kg per day can be employed. Therapy should be initiated at lower doses, the dosage thereafter being increased in very small increments until the desired effect is achieved.

The GABA-T inhibitory activity of the compounds can be demonstrated in laboratory animals in vivo by the methods of M. Jung et al., *J.Neurochem.*, 28, 717 (1977). In human subjects, GABA-T inhibition can be measured after systemic drug administration by determining elevated GABA, homocarnosine, and beta-alanine levels in cerebrospinal fluid (CSF), since there is a known correlation between GABA, homocarnosine and beta-alanine levels in the brain and in CSF.

Biological testing of (R)-allenyl GABA, the enantiomer of (S)-allenyl GABA, has determined that (R)-allenyl GABA is not an irreversible inhibitor of GABA-T. It will be understood that for inhibiting GABA-T and elevating brain GABA levels as hereinabove described, (S)-allenyl GABA can be used either substantially free of (R)-allenyl GABA, or in physical mixture with (R)- allenyl GABA, such as the racemate, (R,S)-allenyl GABA.

It is believed that (S)-allenic GABA and (R,S)-allenic GABA are "substrate-induced irreversible inhibitors" of GABA-T. Such inhibitors are also known in the art as "enzyme-activated irreversible inhibitors", "suicide enzyme inhibitors", "$K_{cat}$ inhibitors", or "mechanism-based inhibitors". In order for a compound to be a substrate-induced irreversible enzyme inhibitor, the compound must be a substrate for the target enzyme, and the compound must contain a latent reactive group susceptible to being unmasked as the result of the normal catalytic action of the enzyme. The unmasking of the latent reactive group by the action of the enzyme generates a reactive function which alkylates a nucleophilic residue present at the active site of the enzyme. Thus, there is formed a covalent bond between the inhibitor and the enzyme at the active site resulting in irreversible inactivation of the enzyme. Such inhibitors are extremely specific since the inhibitor must be a substrate for the target enzyme and since biotransformation of the inhibitor by the target enzyme is required before the enzyme is inactivated. Although it is believed that the (S)-allenyl GABA and (R,S)-allenyl GABA generally exert their action by means of a substrate-induced mechanism, inhibition may occur by other mechanisms, such as by competitive inhibition.

(S)-allenyl GABA and (R,S)-allenyl GABA can be administered in various manners to achieve the desired effect. The compounds can be administered alone or in combination with pharmaceutically acceptable carriers or diluents, the proportion and nature of which are determined by the solubility and chemical properties of the compound selected, the chosen route of administration, and standard pharmaceutical practice. The compounds may be administered orally in solid dosage forms, e.g. capsules, tablets powders, or in liquid forms, e.g. solutions or suspensions. The compounds may also be injected parenterally in the form of sterile solutions or suspensions. Solid oral forms may contain conventional excipients, for instance lactose, sucrose, magnesium stearate, resins, and like materials. Liquid oral forms may contain various flavoring, coloring, preserving, stabilizing, solubilizing, or suspending agents. Parenteral preparations are sterile aqueous or non-aqueous solutions or suspensions which may contain various preserving, stabilizing, buffering, solubilizing, or suspending agents. If desired, additives, such as saline or glucose may be added to make the solutions isotonic.

The amount of novel compound administered will vary and can be any effective amount. Unit doses of these compounds can contain, for example, from about 100 mg to 500 mg of the compounds and may be administered one or more times daily, for example, from 1 to 4 times daily.

As used herein the term patient is taken to mean warm blooded animals, such as, humans and other mammals, for example, cats, dogs, rats, mice, guinea pigs, sheep, horses, and bovine cows.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable diluents or carriers are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

(S)-allenic GABA and (R,S)-allenic GABA can be prepared from an amino-protected derivative of the corresponding (S)- or (R,S)-form of the aminoalkyne compound of Formula I:

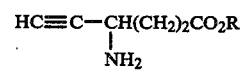

Formula I wherein R is $C_1$–$C_4$ alkyl, by conversion in manner known per se of the ethynyl group into an allenyl group, subsequently freeing the amino group, and converting the ester function into the carboxyl group.

The compounds of Formula I are known per se (see, for example, U.S. Pat. Nos. 3,959,356 and 4,139,563) or can be prepared by analagous methods to known methods.

The amino protecting group will be chosen having regard to the nature of the relevant reaction and ease of removal to free the amino group. The protecting group can be selected from, for example, acyl, for example, lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl (BOC) and the like; carbobenzoxy; benzenesulfonyl; and tosyl. Both amino hydrogen atoms can be substituted by a single protecting group such as, for example phthalyl. The presently preferred protecting group is tert-butoxycarbonyl (BOC). The protection groups are introduced in manner known per se by, for example, reaction of the amine with a lower alkanoyl or aroyl chloride, anhydride or sulfonylchloride. To introduce the BOC group, the compound of Formula I can be treated with tertiobutoxycarbonyloxyimino-2-phenyl-acetonitrile (BOC-ON), di-tertiobutyldicarbonate (BOC)$_2$O) or tertiobutoxycarbonyl chloride.

Removal of the protecting group after the required reaction has been completed can be carried out in manner known per se for the relevant protecting group. Usually, said removal will be by hydrolytic cleavage using a strong organic or mineral acid such as, for example, trifluoroacetic acid, hydrochloric acid and the like acids; or by hydrogen chloride gas under anhydrous conditions. Solvents used will be chosen dependent upon the conditions of protecting group removal. For example, ethers such as, for example, diethylether can be used for cleavage using hydrogen chloride gas.

The conversion of the ethynyl group into the required allenyl group can be carried out by the general method described by P. Crabbé et al (*J.C.S. Chem. Comm.* 1979, 859–860) and H. Fillion et al (*Tet. Letters*, 1980, 929–930) for allenic alcohol. In this method the amino-protected derivative of a compound of Formula I is heated with formaldehyde and a secondary amine having a hydrogen atom on the α-carbon atom in an organic solvent and in the presence of an inorganic salt. Preferably, the heating is under reflux conditions. The preferred amine is di-isopropylamine and the preferred inorganic salt is a copper salt, especially cuprous bromide or cupric chloride. Suitable solvents include dioxane, tetrahydrofuran, 1,2-dimethoxyethane, benzene, acetonitrile and/or toluence.

The conversion is believed to proceed via the corresponding amino protected derivative of the secondary amino propynyl compound, especially the diisopropylamino propynyl compound of the following Formula II

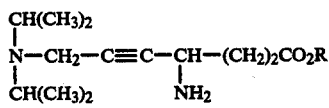

Formula II wherein R is as defined in connection with Formula I.

(S)-Allenyl GABA also can be obtained in manner known per se, for example, by resolution of (R,S)-allenic GABA using a chiral acid, such as (+) or (−) binaphthylphosphoric acid salt by the method described by R. Viterbo et al., in *Tetrahedron Letters* 48, 4617–4620 (1971) and in U.S. Pat. No. 3,848,030 or (+) camphor-10-sulfonic acid.

(S)-4-Amino-hex-5-ynoic acid can be obtained in manner known per se by the resolution of (R,S)-4-amino-hex-5-ynoic acid, for example, using a chiral acid, preferably (+) or (−)-binaphthylphorphoric acid by the method of Viterbo, supra. Use of (+)-binaphthylphosphoric acid is preferred.

The compounds produced by the foregoing processes may be isolated either per se or as salts, usually acid addition salts, thereof.

The acid addition salts are preferably the pharmaceutically acceptable, non-toxic addition salts with suitable acids, such as those previously referred to in this Specification. Apart from pharmaceutically acceptable acid addition salts, other acid addition salts, such as for example, those with picric or oxalic acid are useful; they may serve as intermediates in the purification of the compounds of the invention or in the preparation of other, for example, pharmaceutically acceptable, acid addition salts, or are useful for identification or characterisation of the bases.

A resulting acid addition salt may be converted into the free compound according to known methods, for example, by treating it with an alkali or alkaline earth metal hydroxide or alkoxide, with an alkali or an alkaline earth metal carbonate or hydrogen carbonate, with a trialkylamine; or with an anion exchange resin.

A resulting acid addition salt may also be converted into another acid addition salt according to known methods; for example, a salt with an inorganic acid may be treated with a metal salt, for example a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated by the following non-limiting Examples.

EXAMPLE 1

(R,S)-4-AMINO-HEPTA-5,6-DIENOIC ACID

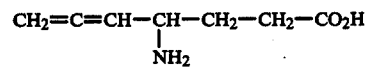

(A) Preparation of:

(R,S)-METHYL-4-(N-TERTIOBUTOXYCARBONYLAMINO)-HEX-5-YNOATE

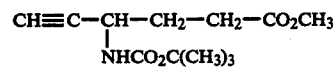

A solution of (R,S)-4-amino-hex-5-ynoic acid (prepared as described in U.S. Pat. No. 3,959,356 (12.7 g, 0.1 mol), in dry methanol is saturated with dry hydrogen chloride gas and allowed to stand overnight at room temperature. The solution is evaporated under reduced pressure to yield the crude (R,S) methyl 4-amino-hex-5-ynoate hydrochloride as residue. This residue is suspended in a solution of ditertiobutyldicarbonate (60 g, 0.1 mol) in chloroform (100 ml). The suspension is cooled to 0° C. and triethylamine (14 ml, 0.1 mol) is added dropwise. The resultant clear solution is heated for 2 hours under reflux, concentrated under reduced pressure, diluted with diethyl ether (200 ml) and washed with water (5×50 ml). The organic layer is dried over magnesium sulfate and concentrated to yield the crude title compound (20 g, 80%). The crude product is purified by crystallisation in diethyl ether/pentane.

(B) Preparation of:

(R,S)-METHYL 4-(N-TERTIOBUTOXYCARBONYLAMINO)-HEPTA-5,6-DIENOATE

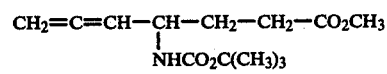

A solution of crude (R,S)-methyl-4-(N-tertiobutoxycarbonyl amino)-hex-5-ynoate prepared as in Step A (4.8 g, 0.02 mol), formaldehyde (2.7 ml of 37% aqueous solution, 0.036 mol), diisopropylamine (3.2 ml, 0.025 mol) and cuprous bromide (1 g, 0.006 mol) in dioxane (50 ml) is heated under reflux for 2 hours. The solution is quenched with 1N aqueous acetic acid (50 ml) and extracted with diethyl ether. The organic layer is dried over magnesium sulfate and concentrated under reduced pressure. The residue is purified by column chromatography on silica gel using diethyl ether:petroleum ether (50:50) as eluant to yield the title compound (2.2 g).

(C) Preparation of:

(R,S)-4-AMINO-HEPTA-5,6-DIENOIC ACID, HYDROCHLORIDE

A solution of (R,S)-methyl 4-(N-tertiobutoxycarbonylamino)-hepta-5,6-dienoate prepared as in Step B (1.275 g, 0.005 mol) and lithium hydroxide (0.12 g, 0.005 mol) in dimethoxyethane (10 ml) and water (3 ml) is allowed to stand at room temperature for 3 hours. The solution is diluted with diethyl ether and water and the organic layer acidified with 0.01 N aqueous hydrochloric acid, saturated with sodium chloride and extracted with diethyl ether. The resulting organic layer is dried over magnesium sulfate and concentrated under reduced pressure and the residue recrystallised from ether/pentane to yield (R,S)-4-(N-tertiobutoxycarbonylamino) hepta-5,6-dienoic acid (1.1 g). This acid is added to a saturated solution of dry hydrogen chloride in dry diethyl ether (20 ml) and left overnight at room temperature. The hydrochloride is formed directly as crystals, filtered, washed with diethyl ether and dried to provide the pure title compound in nearly quantitative yield (0.7 g, m.p. 112° C.).

(D) Preparation of:

(R,S)-4-AMINO-HEPTA-5,6-DIENOIC ACID (R,S)-4-Amino-hepta-5,6-dienoic acid hydrochloride obtained as in Step C above is neutralized with 1 equivalent of triethylamine in ethanol. After concentration under reduced pressure, the residue is taken up with chloroform. The insoluble material is recrystallized from ethanol:water.

EXAMPLE 2

(S)-4-AMINO-HEPTA-5,6-DIENOIC ACID

The procedure of Example 1 is repeated commencing with (S)-4-amino-hex-5-ynoic acid to yield (S)-4-amino-hepta-5,6-dienoic acid (mp 170° C. $[\alpha]_D = +44°$, C=0.25/H$_2$O) via the intermediate (S)-4-(N-tertiobutoxycarbonylamino)-hepta-5,6-dienoic acid (mp 79° C. $[\alpha]_D = -61.2°$, C=0.25/CHCl$_3$).

Similarly the R-isomer (mp 169° C., $[\alpha]_D = -38°$, C=0.25/H$_2$O) is prepared from (R)-4-amino-hex-5-ynoic acid via the intermediate (R)-4-(N-tertio-butoxycarbonylamino) hepta-5,6-dienoic acid (mp 69° C. $[\alpha]_D = +68.80°$, C=0.25/CHCl$_3$).

In biochemical tests the (S)(+) isomer was found to be an irreversible inhibitor of GABA-T. The (R)(−)-isomer was not active.

EXAMPLE 3

The ability of (S)-allenyl GABA and (R,S)-allenyl GABA to inhibit GABA-T enzyme and to increase GABA levels in the brain can be demonstrated in the following test procedures in mice.

Male albino CD1 mice each weighing approximately 34 g at commencement of the test are given an i.p. injection of the test compound in aqueous solution daily for seven consecutive days. Half of the animals are killed by decapitation 24 hours after the last dose fo the test compound. The other half of the animals are observed for up to 12 days for toxicity (as indicated by weight loss and deaths). Control animals receive an injecion of the vehicle only.

The brains are removed from the dead mice and are divided into two portions by sagittal section. One half is used for the measurement of GABA-T activity while the other is used for measuring GABA content. The GABA-T activity is measured using known methods as described by M. Jung et al., *J.Neurochem.*, 28, 717 (1977) and 29, 797 (1977). GABA content is measured by perchloric acid or trichloroacetic acid extracts using an amino acid analyzer equiped with a fluorescence detector.

When tested as described above (R,S)-allenyl GABA gave the results set forth in Table 1 below.

TABLE 1

| Compound | Daily Dose (mg/kg) | GABA—T Activity+ | GABA Level++ |
|---|---|---|---|
| (R,S)—Allenyl GABA | 50* | 55 | 130 |
| (R,S)—Allenyl GABA | 100* | 74 | 180 |

*No obvious sign of toxicity, no weight loss and no gross behavioural changes at the 50 or 100 mg/kg/day doses of allenyl GABA.
+Calculated as percent inhibition.
++Calculated as percent of control.

EXAMPLE 4

A. The procedure of Example 3 is repeated using a single i.p. dose of the test compound and killing the mice 6 hours after the i.p. injection. The results for (S)-allenyl GABA ("S") and (R,S)-allenyl GABA ("R,S") are set forth in Table 2 below.

TABLE 2

| Compound | mM/kg | Dose (mgs/kg) | GABA—T Activity+ | GABA Level++ |
|---|---|---|---|---|
| (R,S) | 1.55 | 273.5 | 76 | 470 |
|  | 3.10 | 547.2 | 89 | 530 |
|  | 6.2 | 1094.3 | 96 | 770 |
| (S) | 0.77 | 135.9 | 79 | 540 |
|  | 1.55 | 273.5 | 92 | 670 |
|  | 3.10 | 547.2 | 96 | 730 |

+Calculated as percent inhibition.
++Calculated as percent of control.

The results in Table 2 demonstrate that (S)-allenyl GABA has twice the potency of (R,S)-allenyl GABA for the elevation of GABA levels.

B. The procedure of Part A is repeated using both oral and i.p. doses of (R,S)-allenyl GABA. The results are set forth in Table 3 below:

TABLE 3

| Mode of Administration | Dose mM/kg | (mg/kg) | GABA—T Activity+ | GABA Level++ |
|---|---|---|---|---|
| i.p. | 0.77 | 135.9 | 64 | 310 |
|  | 1.94 | 342.4 | 84 | 490 |
|  | 3.87 | 683.1 | 88 | 600 |
| oral | 0.77 | 135.9 | 69 | 330 |
|  | 1.94 | 342.4 | 81 | 434 |
|  | 3.87 | 683.1 | 86 | 530 |

+Calculated as percent inhibition.
++Calculated as percent of control.

The results in Table 3 indicate that within minor differences due to biological variations, (R,S)-allenyl GABA and (S)-allenyl GABA are equally effective when given by the oral and i.p. routes of administration.

EXAMPLE 5

A. The toxicity of (S)-allenyl GABA and (R,S)-allenyl GABA was determined after i.p. administration to male mice. The mice were observed up to eight days after injection. The lethality of the compounds (given as the number of dead animals per group) is set forth below:

| Compound | Dose (mg/kg) | No. of dead animals Day | | | | |
|---|---|---|---|---|---|---|
| | | 1 | 2 | 3 | 4 | 8 |
| (R,S)—allenyl GABA | 500 | 0/5 | 0/5 | 0/5 | 0/5 | 0/5 |
| | 750 | 3/5 | 3/5 | 3/5 | 3/5 | 3/5 |
| | 1000 | 2/5 | 4/5 | 5/5 | — | — |
| | 1500 | 5/5 | — | — | — | — |
| (S)—allenyl GABA | 250 | 0/5 | 0/5 | 0/5 | 0/5 | 0/5 |
| | 375 | 0/5 | 0/5 | 0/5 | 0/5 | 0/5 |
| | 500 | 0/5 | 0/5 | 0/5 | 0/5 | 0/5 |
| | 750 | 0/5 | 0/5 | 0/5 | 0/5 | 0/5 |

The above results indicate that (S)-allenyl GABA is non-toxic after i.p. administration of very large doses corresponding to maximal biological effects. (R,S)-allenyl GABA, however, is toxic at doses that are about 4–5 times higher than the lowest biochemical effective dose.

B. The toxicity of (S)-allenyl GABA ("S") and (R,S)-allenyl GABA ("R,S") was determined as in Part A after both oral and i.p. administration. The lethality of the compounds on day 4 after injection (given as the number of dead animals per group) is set forth below:

| Compound | Mode of Administration | Dose (mg/kg) | No. of dead animals Day 4 |
|---|---|---|---|
| (R,S) | i.p. | 500 | 0/5 |
| | | 750 | 3/5 |
| | | 1000 | 5/5 |
| | | 1500 | 5/5 |
| (R,S) | oral | 500 | 0/5 |
| | | 750 | 0/5 |
| | | 1000 | 0/5 |
| | | 1500 | 0/5 |
| (S) | oral | 500 | 0/5 |
| | | 750 | 1/5 |

The above data indicate that (R,S)-allenyl GABA did not show toxicity by the oral route up to a dose of 1500 mg/kg. The data also indicate that (S)-allenyl GABA is non-toxic by oral administration.

EXAMPLE 6

The ability of (R,S)-allenyl GABA to protect mice against seizures and death induced by mercaptopropionic acid was demonstrated as follows:

Mice (3.5) were given a single i.p. injection of the test compound. Six hours later the animals received mercaptopropionic acid at a dose of 53 mg/kg i.p. The animals were observed for the appearance of clonic toxic seizures and death. The results of the testing are set forth below

| Dose (mMole/kg) | Number of Dead animals | Number of Animals having seizures |
|---|---|---|
| 0 | 3/5 | 5/5 |
| 0.39 | 3/5 | 5/5 |
| 0.77 | 2/5 | 5/5 |
| 1.9 | 0/5 | 3/5 |
| 3.9 | 0/5 | 3/5 |

While (R,S)-allenyl GABA does not protect totally against seizures in this model, (R,S)-allenyl GABA significantly reduces the number of dead animals.

EXAMPLE 7

An illustrative composition for hard gelatin capsules is as follows:

| (a) (S)— or (R,S)—allenyl GABA | 200 mg |
|---|---|
| (b) talc | 35 mg |

The formulation is prepared by passing the dry powders of (a) and (b) through a fine mesh screen and mixing them well. The powder is then filled into hard gelatine capsules at a net fill of 235 mg per capsule.

EXAMPLE 8

An illustrative composition for tablets is as follows:

| (a) (S)— or (R,S)—allenyl GABA | 100 mg |
|---|---|
| (b) wheat starch | 15 mg |
| (c) lactose | 33.5 mg |
| (d) magnesium stearate | 1.5 mg |

A portion of the wheat starch is used to make a granulation which together with the remainder of the wheat starch and the lactose is granulated, dried, screened, and mixed with the active compound (a) and the magnesium stearate. The mixture is compressed into tablets weighing 150 mg each.

EXAMPLE 9

An illustrative composition for a parenteral injection is the following wherein the quantities are on a weight to volume basis:

| | Amount |
|---|---|
| (a) (S)— or (R,S)—allenyl GABA | 100.0 mg |
| (b) sodium chloride | q.s. |
| (c) water for injection to make | 20 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules each containing 5 mg of the active ingredient for single dosage.

EXAMPLE 10

| | mg/suppository |
|---|---|
| (S)— or (R,S)—allenyl GABA | 200 |
| Oil of Theobroma | 800 |

The medicament is powdered and passed through a B.S. No. 100 Sieve and triturated with molten oil of Theobroma at 45° C. to form a smooth suspension. The mixture is well stirred and poured into moulds each of nominal 1 G capacity, to produce suppositories.

What is claimed is:

1. (S)-4-Amino-hepta-5,6-dienoic acid or a pharmaceutically acceptable salt thereof.
2. (R,S)-4-Amino-hepta-5,6-dienoic acid or a pharmaceutically acceptable salt thereof.
3. A pharmaceutical composition comprising a compound as claimed in claim 1 and a pharmaceutically acceptable carrier or diluent thereof.
4. A pharmaceutical composition comprising a compound as claimed in claim 2 and a pharmaceutically acceptable carrier or diluent therefor.

5. A method of inhibiting GABA-T in a patient in need thereof which comprises administering to the patient a GABA-T inhibiting amount of a compound as claimed in claim 1.

6. A method of inhibiting GABA-T in a patient in need thereof which comprises administering to the patient a GABA-T inhibiting amount of a compound as claimed in claim 2.

* * * * *